United States Patent [19]
Bach et al.

[11] Patent Number: 4,808,758
[45] Date of Patent: Feb. 28, 1989

[54] HYDROFORMYLATION PROCESS

[75] Inventors: Hanswilhelm Bach, Duisburg; Boy Cornils, Hofheim; Wilhelm Gick, Duisburg; Heinz-Dieter Hahn, Oberhausen; Werner Konkol, Oberhausen; Ernst Wiebus, Oberhausen, all of Fed. Rep. of Germany

[73] Assignee: Ruhrchemie Aktiengesellschaft, Fed. Rep. of Germany

[21] Appl. No.: 125,596

[22] Filed: Nov. 25, 1987

[30] Foreign Application Priority Data

Nov. 27, 1986 [DE] Fed. Rep. of Germany ....... 3640614

[51] Int. Cl.⁴ ............................................. C07C 45/50
[52] U.S. Cl. ..................................... 568/454; 568/451
[58] Field of Search ................. 568/454, 492, 909, 451

[56] References Cited
U.S. PATENT DOCUMENTS
4,547,595 10/1985 Chang ................................ 568/454

FOREIGN PATENT DOCUMENTS
0096987 12/1983 European Pat. Off. ............ 568/454
2627354 12/1976 Fed. Rep. of Germany ...... 568/454

Primary Examiner—Werren B. Lone
Attorney, Agent, or Firm—Bierman & Muserlian

[57] ABSTRACT

In a hydroformylation process for the preparation of aldehydes by reacting aliphatic olefins of 2 to 12 carbon atoms with carbon monoxide and hydrogen at temperatures of 20° to 150° C. and pressures of 0.1 to 20 mPa in the liquid phase and in the presence of an aqueous solution of a catalyst containing originally 50 to 800 wt. ppm of rhodium and 25 to 30 wt. % of complex-forming, sulfonated or carboxylated triarylphosphines, in each case based on the aqueous solution, the improvement comprising adding fresh phosphine solution to maintain the original phosphine concentration, until the total concentration of complex-forming phosphines and secondary and degradation products of the phosphines not capable of forming complexes amounts to about 35 to 45 wt. % based on the aqueous solution to selectively form n-aldehydes.

8 Claims, 1 Drawing Sheet

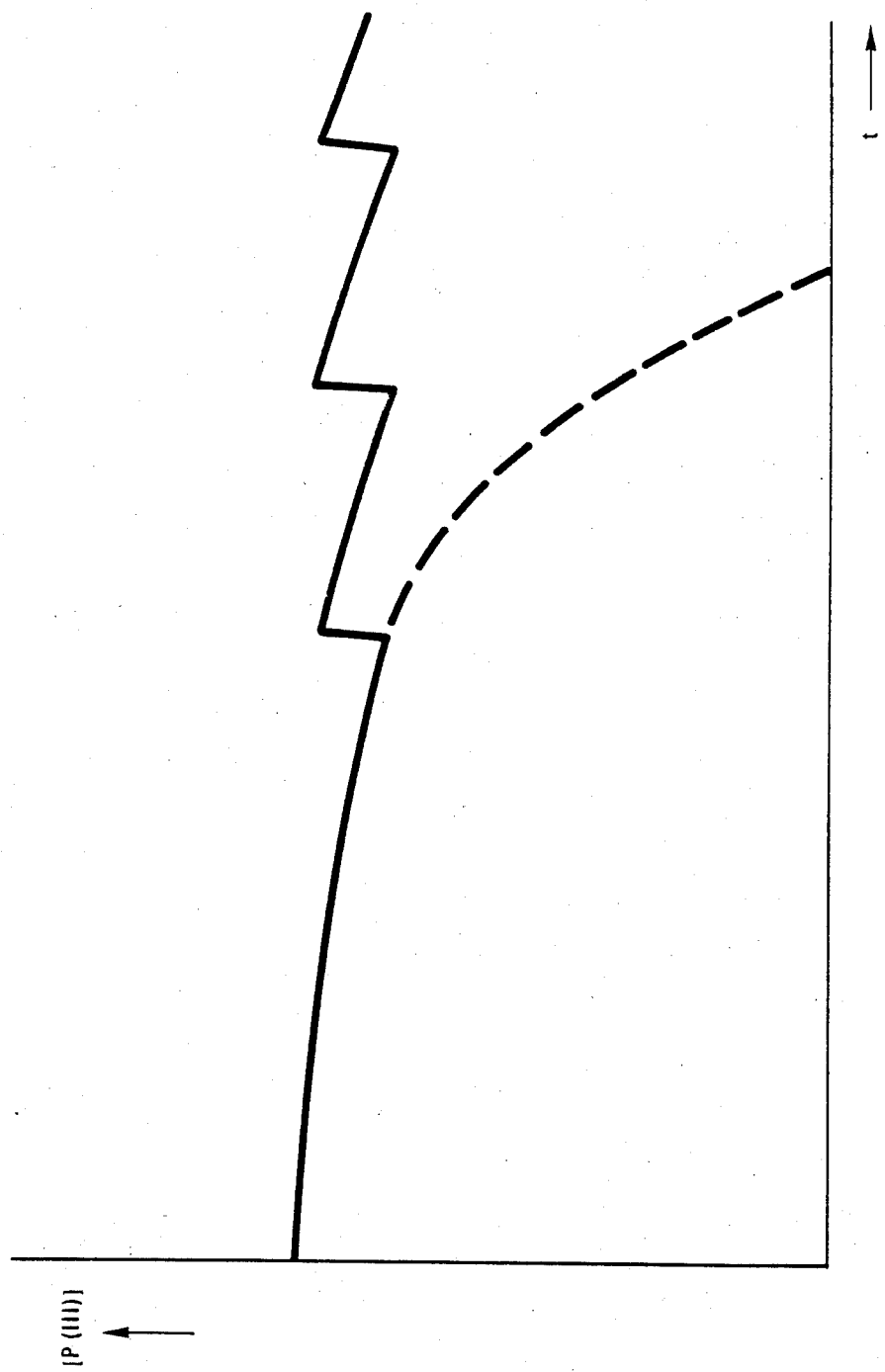

HYDROFORMYLATION PROCESS

STATE OF THE ART

DE No. 2,627,354 describes a process for the preparation of aldehydes by reacting aliphatic olefins of 2 to 20 carbon atoms with carbon monoxide and hydrogen in the liquid phase in the presence of water as well as rhodium in metallic form or in the form of one of its compounds, an aryl phosphine and alkali metal, alkaline earth metal or ammonium ions which is characterized in that the reaction is performed in aqueous solution in the presence of a water-soluble, sulfonated aryl or naphthylphosphine DE No. 3,135,127 describes the use of compounds containing carboxyl groups in the aryl or naphthyl groups as water-soluble phosphines.

The hydroformylation of olefins in the presence of an aqueous catalyst phase has a number of advantages. For example, with this process variant, the catalyst is separated from the reaction product after completion of the hydroformylation reaction simply be separation of the organic and aqueous phases, i.e. without distillation and thus without additional thermal loading of the reaction products. Furthermore, the process is characterized by high selectivity towards the formation of n-compounds rather than iso compounds so that the reaction product formed during the hydroformylation of propylene contains about 95 wt. % n-butyraldehyde and only 5 wt. % iso-butyraldehyde, which is less in demand for further use. Finally, poisoning of the catalyst by high-boiling by-products formed e.g. by aldolization or aldol condensation or acetal formation is largely avoided.

The reaction of the olefin with carbon monoxide and hydrogen takes place in the aqueous catalyst-containing phase and according to the German Patent Application No. 3,546,123.3, the catalyst solution contains 450 to 800 wt. ppm of rhodium and 25 to 30 wt. % of sulfonated or carboxylated triarylphosphine, in each case based on the aqueous solution. The ratio of rhodium to phosphine (in g-atom per gram molecule) is normally 1:10 to 300, preferably 1:50 to 150.

A measure for the effectiveness of the catalyst system consisting of rhodium and water-soluble ligands is the number of gram molecules of aldehyde whicha re formed per volume unit of catalyst solution and per time unit. In the following, the term "productivity" is used to describe this relation, i.e.

$$\text{Productivity} = \frac{\text{gram molecules of aldehyde}}{\text{l catalyst solution} \times h}$$

Productivity is increased with increasing amounts of rhodium in the aqueous catalyst solution and both the rhodium concentration and the stability of the sulfonated or carboxylated triarylphosphines is influenced. With increasing rhodium concentration, the tendency of the carbon-phosphorus bond to split increases, e.g. forming substituted phosphinic acid derivatives, aryl sulfonates or aryl carboxylates. This reaction results in a decrease in the selectivity of the catalyst system and increased formation of iso compounds. Furthermore, the decrease in selectivity may also be indicated by the fact that more alcohols and higher-boiling condensation products are formed.

The productivity of the catalyst system not only depends on the rhodium concentration but also on the concentration of sulfonated or carboxylated triarylphosphines in the catalyst solution. An increase in the phosphine proportion in the aqueous phase to over 28 wt. %, and in particular to over 30 wt. %, based on the aqueous solution leads to a fall in the rate of the hydroformylation reaction and thus to a decrease in the productivity of the catalyst system.

Even when the rhodium and phosphine concentrations mentioned in German Patent Application No. 3,546,123.3 are maintained, the phosphines are transformed over the course of time by splitting the carbon-phosphorus bonds and also by oxidation. The phosphine concentration falls with the results previously described that, when catalyst solutions already in use for some time are employed, the n/iso ratio of the products in the reaction mixture shifts in favor of the iso compounds. Therefore, it is necessary to replace the catalyst solution at certain intervals.

OBJECTS OF THE INVENTION

It is an object of the invention to provide an improved hydroformylation reaction with the original activity and selectivity over a prolonged period of time.

This and other objects and advantages of the invention will become obvious from the following detailed description.

THE INVENTION

The novel process of the invention for the preparation of aldehyde by reacting aliphatic olefins of 2 to 12 carbon atoms with carbon monoxide and hydrogen at temperatures of 20 to 150° C. and pressures of 0.1 to 20 mPa in the liquid phase and in the presence of an aqueous solution as a catalyst containing originally 50 to 800, preferably 200 to 600 wt. ppm of rhodium and 25 to 30 wt. of complex-forming, sulfonated or carboxylated triarylphosphines, in each case based on the aqueous solution is characterized in that, to maintain the original phosphine concentration, fresh phosphine solution is added until the total concentration of complex-forming phosphines and secondary and degradation products of the phosphines not capable of forming complexes amounts to about 35 to 45 wt. % based on the aqueous solution.

The procedure of the invention ensures that the effectiveness of the catalyst does not differ at all, or if so, only slightly from that of a fresh catalyst even after long use. The term "effectiveness" is understood to mean above all the productivity and the selectivity of the catalyst. In particular, it could not have been foreseen that with a catalyst solution used over a long period, the total concentration of phosphines and phosphine secondary and degradation products can be raised to values above 25 to 30 wt. %. As already mentioned, with fresh catalyst solutions phosphine concentrations which exceed the afore-mentioned range lead to an appreciable decrease in the productivity of the catalyst system. However, its productivity is also reduced by salts such as $Na_2SO_4$ contained in the fresh catalyst solution but inert with regard to the reaction.

Therefore, if two fresh catalyst solutions contain rhodium and phosphine in the same concentrations, the phosphines being in the range of 25 to 30 wt. %, and if other salts are also dissolved in one of these solutions so that the total concentration of dissolved salts exceeds 25 to 30 wt. %, this concentrated solution exhibits a lower productivity than the other less concentrated one. In this connection, it was surprising that secondary products of the water-soluble phosphine which are present in the catalyst solutions and which have been formed through degradation, rearrangement and other reactions, in contrast to e.g. $Na_2SO_4$, do not reduce the productivity of the catalyst solution, even if the total concentration of all dissolved substances exceeds the range of 25 to 30 wt. % through their presence.

The water-soluble, sulfonated or carboxylated phosphine ligands have the formula

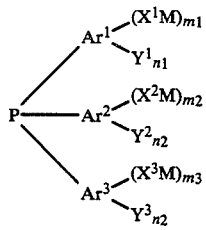

wherein $Ar^1$, $Ar^2$, $Ar^3$ individually are phenyl or naphthyl, $Y^1$, $Y^2$, $Y^3$ individually are a straight-chain or branched alkyl or alkoxy of 1 to 4 carbon atoms, halogen, —OH, —CN, —$NO_2$ or $R^1R^2N$ wherein $R^1$ and $R^2$ individually are straight-chain or branched alkyl of 1 to 4 carbon atoms; $X^1$, $X^2$, $X^3$ are individually carboxylate —(COO $-$) and/or sulfonate —($SO_3^-$), $m_1$, $m_2$, $m_3$ are individually whole numbers from 0 to 3, at least one of $m_1$, $m_2$, or $m_3$ being equal to or greater than 1; $n_1$, $n_2$, $n_3$ are individually whole numbers from 0 to 5, M is an alkali metal ion, an equivalent of an alkaline earth metal or zinc ion, an ammonium or quaternary ammonium ion of the formula —$N(R^3R^4R^5R^6)^+$, wherein $R^3$, $R^4$, $R^5$, $R^6$ individually are a straight-chain or branched alkyl of 1 to 18 carbon atoms or aralkyl of 7 to 14 carbon atoms. Quaternary ammonium groups where three of the groups $R^3$, $R^4$, $R^5$, $R^6$ individually have 1 to 4 carbon atoms and the fourth group is an aralkyl of 7 to 14 carbon atoms have proved particularly useful.

Water-soluble triarylphosphines of the above formula are preferred wherein $Ar^1$, $Ar^2$, $Ar^3$ are phenyl, $m_1$, $m_2$, $m_3$ denote 0 or 1 and the sum of $m_1+m_2+m_3$ is 2 or 3 and $n_1$, $n_2$ and $n_3$ are 0. Examples of compounds of the said formula are triphenylphosphine trisodium trisulfonate, triphenylphosphine tri(tetraalkylammonium) trisulfonate, triphenylphosphine trisodium tricarboxylate, triphenylphosphine disodium disulfonate.

the sulfonated or carboxylated arylphosphines can be used as single compounds but, phosphine mixtures containing different numbers of sulfonate or carboxylate groups can also be used, i.e. mixtures of salts of triarylphosphine trisulfonic acids and triarylphosphine disulfonic acids. Moreover, the sulfonates or carboxylates need not contain the same cation. Mixtures of salts derived from different metals and/or containing ammonium and/or quaternary alkylammonium ions are suitable.

The catalyst systems consisting of a rhodium complex compound and excess water-soluble phosphines is used as an aqueous solution containing 50 to 800 wt. ppm of rhodium and 25 to 30 wt. % of water-soluble phosphine, in each case based on the solution. It has proved particularly useful to work with solutions containing 200 to 600 wt. ppm of rhodium and 26 to 28 wt. % of water-soluble phosphine.

The original catalyst solution is understood to be a freshly prepared solution which does not yet contain any phosphine secondary or degradation products or a used solution which contains phosphine and degradation products in such a small concentration that its original effectiveness, characterized particularly by its productivity and the ratio of n to iso compounds in the reaction product, has not altered.

If the effectiveness of the catalyst solution diminishes, water-soluble phosphine is added until the original state is attained again. Naturally, any level between the original state and the current state can be attained in this manner and it is irrelevant which reference is selected to evaluate the effectiveness of the catalyst system. For example, the selective formation of n and iso compounds in the reaction product or the proportion of alcohols or higher-boiling condensation products can be used. It is also possible to take several features, e.g. two or three, to evaluate the state of the catalyst.

The water-soluble phosphine can be added to the catalyst solution as a solid or as an aqueous solution and the concentration of the phosphine in the aqueous solution can be freely selected within a wide range. It has proved useful to employ solutions containing 25 to 35 wt. % of phosphine. The phosphine added to the catalyst system does not need to be the same as the one already contained in the catalyst solution and they can differ in their cations or anions or both in their cations and anions. Thus, the corresponding potassium salt or a tetraalkylammonium salt or a salt of the triphenylphosphine disulfonic acid can be added to a solution which originally only contained triphenylphosphine trisodium trisulfonate and the salt can be added continuously or discontinuously. A graph curve of the phosphine concentration characteristic for the discontinuous mode of operation is shown in the enclosed FIGURE.

The addition of phosphine to the catalyst solution can be continued until the total concentration of phosphine and phosphine secondary and degradation products is about 35 to 45 wt %, in particular 40 to 45 wt. %, based on the aqueous solution. Any further addition of phosphine cannot return the catalyst solution to its original effectiveness. After the maximum total concentration has been attained as when the selectivity falls, the catalyst solution can be worked up either as a whole or by continuous removal of parts of the solution.

A suitable work-up process is, for example, the extraction of the previously acidified solution with a solution of an amine in an organic solvent and subsequent treatment of the organic phase with the aqueous solution of an inorganic base. According to another procedure, the rhodium complex compound and phosphines including their transformation product are separated using a membrane separation process. The rhodium complex compound can be used immediately again as a catalyst component while the phosphine is recovered by extraction with amine.

According to the process of the invention, olefins of 2 to 12 carbon atoms can be hydroformylated and these olefins can be linear or branched and contain a terminal or internal double bond. Cycloolefins of 6 to 12 carbon atoms can also be used. Examples of the olefins described above are ethylene, propylene, i-butene, 2-butene, 1-pentene, 2-methyl-1-butene, 4,4-dimethyl-1-nonene,1-dodecene, cyclohexene and dicyclopentadiene. It is preferable to use linear olefins of 2 to 8 carbon atoms such as ethylene, propylene, 1-butene, 1-pentene, 1-hexene, 1-heptene and 1-octene or in the case of cycloolefins, dicyclopentadiene.

The total pressure of hydrogen and carbon monoxide amounts to 0.1 to 20 mPa, preferably 1 to 10 mPa. The composition of the synthesis gas, i.e. the ratio of carbon monoxide to hydrogen can be varied within wide limits and generally synthesis gas is added in which the volume ratio of carbon monoxide to hydrogen is 1:1 or only deviates slightly from this value. The reaction takes place at temperatures of 20° to 150° C. and it can be carried out continuously or batchwise.

In the following examples there are described several preferred embodiments to illustrate the invention. However, it should be understood that the invention is not intended to be limited to the specific embodiments.

EXAMPLE 1

(Comparative Example)

Propylene, carbon monoxide and hydrogen in a volume ratio of 1:1:1 were added to an aqueous catalyst solution containing 27 wt. % of a mixture of the sodium salts of triphenylphosphine trisulfonic acid and triphenylphosphine disulfonic acid and 500 wt. ppm of rhodium, in each case based on the solution, at a temperature of 122° C. and a pressure of 5 mPa. 1.95 gram molecules of a mixture of 95% n- and 5% iso-butyraldehyde were obtained per liter of catalyst solution and per hour. Over the course of time, the phosphine ligand gradually degraded and the selectivity of the reaction diminished.

EXAMPLE 2

Example 1 was repeated and as soon as slight selectivity losses were observed, i.e. at a phosphine/rhodium ratio of 90:1 (gram molecule : g atom), enough fresh ligand was added to attain the original phosphine/rhodium ratio. This procedure was repeated without a reduction in productivity until the total concentration of phosphine and phosphine secondary and degradation products was 45 wt. % based on the solution. During the entire time, an aldehyde mixture with a constant composition (95% n and 5% iso-compounds) was obtained.

Various modifications of the processes may be made without departing from the spirit or scope thereof and it is to be understood that the invention is intended to be limited only as defined in the appended claims.

What we claim is:

1. In a hydroformylation process for the preparation of aldehydes by reacting aliphatic olefins of 2 to 12 carbon atoms with carbon monoxide and hydrogen at temperatures of 20° to 150° C. and pressures of 0.1 to 20 mPa in the liquid phase and in the presence of an aqueous solution of a catalyst containing originally 50 to 800 wt. ppm of rhodium and 25 to 30 wt. % of complex-forming, sulfonated or carboxylated triarylphosphines, in each case based on the aqueous solution, the improvement comprising adding fresh phosphine solution to maintain the original phosphine concentration until the total concentration of complex-forming phosphines and secondary and degradation products of the phosphines not capable of forming complexes amounts to about 35 to 45 wt. % based on the aqueous solution.

2. The process of claim 1 wherein the water-soluble phosphine of the catalyst solution is added as a solid.

3. The process of claim 1 wherein the water-soluble phosphine of the catalyst solution is added as an aqueous solution.

4. The process of claim 3 wherein the aqueous solution contains 26 to 28 wt. % phosphine based on the solution.

5. The process of claim 1 wherein the water-soluble phosphine is added continuously.

6. The process of claim 1 wherein the water-soluble phosphine is added discontinuously to the catalyst solution.

7. The process of claim 1 wherein the total concentration of complex-forming phosphines and secondary and degradation products of the phosphines not capable of forming complexes finally amounts to 40 to 45 wt. % based on the aqueous solution.

8. The process of claim 1 wherein the rhodium is 200 to 600 wt. ppm.

* * * * *